(12) United States Patent
Han

(10) Patent No.: US 11,100,632 B2
(45) Date of Patent: Aug. 24, 2021

(54) IMAGE SYNTHESIS USING ADVERSARIAL NETWORKS SUCH AS FOR RADIATION THERAPY

(71) Applicant: Elekta, Inc., Atlanta, GA (US)

(72) Inventor: Xiao Han, Maryland Heights, MO (US)

(73) Assignee: Elekta, Inc., Atlanta, GA (US)

( * ) Notice: Subject to any disclaimer, the term of this patent is extended or adjusted under 35 U.S.C. 154(b) by 165 days.

(21) Appl. No.: 15/952,686

(22) Filed: Apr. 13, 2018

(65) Prior Publication Data
US 2019/0318474 A1    Oct. 17, 2019

(51) Int. Cl.
*G06T 7/00*    (2017.01)

(52) U.S. Cl.
CPC .. *G06T 7/0012* (2013.01); *G06T 2207/10081* (2013.01); *G06T 2207/10088* (2013.01); *G06T 2207/20081* (2013.01)

(58) Field of Classification Search
CPC ......... G06T 7/0012; G06T 2207/10081; G06T 2207/10088; G06T 2207/20081; G06K 9/6267
USPC ........................................................ 382/128
See application file for complete search history.

(56) References Cited

U.S. PATENT DOCUMENTS

| 10,592,779 | B2 * | 3/2020 | Madani | G06N 3/0481 |
| 2016/0114192 | A1 * | 4/2016 | Lachaine | A61N 5/1037 600/1 |
| 2019/0188870 | A1 * | 6/2019 | Park | G06K 9/0014 |
| 2019/0259493 | A1 * | 8/2019 | Xu | G06K 9/34 |
| 2019/0304157 | A1 * | 10/2019 | Amer | G06N 3/0445 |

(Continued)

FOREIGN PATENT DOCUMENTS

| CN | 111971689 A | 11/2020 |
| WO | WO-2019199699 A1 | 10/2019 |
| WO | WO-2019209820 A1 | 10/2019 |

OTHER PUBLICATIONS

U.S. Appl. No. 16/044,245, filed Jul. 24, 2018, Cone-Beam CT Image Enhancement Using Generative Adversarial Networks.

(Continued)

*Primary Examiner* — Amandeep Saini
(74) *Attorney, Agent, or Firm* — Schwegman Lundberg & Woessner, P.A.; Sanjay Agrawal

(57) ABSTRACT

A statistical learning technique that does not rely upon paired imaging information is described herein. The technique may be computer-implemented and may be used in order to train a statistical learning model to perform image synthesis, such as in support of radiation therapy treatment planning. In an example, a trained statistical learning model may include a convolutional neural network established as a generator convolutional network, and the generator may be trained at least in part using a separate convolutional neural network established as a discriminator convolutional network. The generator convolutional network and the discriminator convolutional network may form an adversarial network architecture for use during training. After training, the generator convolutional network may be provided for use in synthesis of images, such as to receive imaging data corresponding to a first imaging modality type, and to synthesize imaging data corresponding to a different, second imaging modality type.

20 Claims, 9 Drawing Sheets

(56) References Cited

U.S. PATENT DOCUMENTS

2019/0333219 A1    10/2019    Xu et al.

OTHER PUBLICATIONS

"International Application Serial No. PCT US2019 026400, International Search Report dated Jun. 14, 2019", 4 pgs.
"International Application Serial No. PCT US2019 026400, Written Opinion dated Jun. 14, 2019", 8 pgs.
"International Application Serial No. PCT US2019 028710, International Search Report dated Aug. 22, 2019", 4 pgs.
"International Application Serial No. PCT US2019 028710, Written Opinion dated Aug. 22, 2019", 5 pgs.
Chartsias, Agisilaos, "Adversarial Image Synthesis for Unpaired Multi-modal Cardiac Data", Image Analysis and Recognition : 11th International Conference, ICIAR 2014, Vilamoura, Portugal, (Sep. 26, 2017), 1-11.
Dong, Nie, "Medical Image Synthesis with Context-Aware Generative Adversarial Networks", Arxiv.Org, Cornell University Library, 201 Olin Library Cornell University Ithaca, NY 14853, (Dec. 16, 2016), 12 pgs.
Matteo, Maspero, "Fast synthetic CT generation with deep learning for general pelvis MR-only Radiotherapy", Arxiv.Org, Cornell University Library, 201 Olin Library Cornell University Ithaca, NY 14853, (Feb. 19, 2018), 14 pgs.
Nie, Dong, "Estimating CT Image from MRI Data Using 3D Fully Convolutional Networks", (Sep. 27, 2016), 9 pgs.
"International Application Serial No. PCT US2017 043479, International Search Report dated Nov. 21, 2017", 3 pgs.
"International Application Serial No. PCT US2017 043479, Written Opinion dated Nov. 21, 2017", 6 pgs.
Jin, Kyong, "Deep Convolutional Neural Network for Inverse Problems in Imagin", IEEE Transactions on Image Processing Publication of the IEEE Signal Processing Society, (Jun. 15, 2017).
Qingsong, Yang, "Ct Image Denoising with Perceptive Deep Neural Networks", Arxiv.Org Cornell University Library 201 Olin Library Cornell University Ithaca NY, (Feb. 22, 2017).
Schulze, R, "Artefacts in CBCT: a review", Dentomaxillofacial Radiology, (2011), 265-273.
Wurfl, Tobias, "Deep Learning Computed Tomography", Network and Parallel Computing Notes in Computer Science Lect.Notes Computer Springer International Publishing CHAM, (Oct. 2, 2016), 432-440.
Gauthier, Jon, "Conditional generative adversarial nets for convolutional face generation", Class Project for Stanford CS231N: Convolutional Neural Networks for Visual Recognition, Winter semester 2014.5, (2014), 9 pgs.
Isola, Phillip, et al., "Image-to-Image Translation with Conditional Adversarial Networks", (Nov. 22, 2017), 18 pgs.
Wolterink, Jelmer M., et al., "Deep MR to CT Synthesis using Unpaired Data", (Aug. 3, 2017), 10 pgs.
Zhu, Jun-Yan, et al., "Unpaired Image-to-Image Translation using Cycle-Consistent Adversarial Networks", [Online]. Retrieved from the Internet: <URL: https://junyanz.github.io/CycleGAN/, (Accessed Mar. 1, 2018), 8 pgs.
Zhu, Jun-Yan, et al., "Unpaired Image-to-Image Translation using Cycle-Consistent Adversarial Networks", (Feb. 1, 2018), 21 pgs.
Zhu, Jun-Yan, "Unpaired Image-to-Image Translation using Cycle-Consistent Adversarial Networks", Berkeley AI Research (BAIR) laboratory, UC Berkeley, (Feb. 19, 2018), 20 pgs.
"International Application Serial No. PCT/US2019/026400, International Preliminary Report on Patentability dated Oct. 22, 2020", 10 pgs.
"International Application Serial No. PCT/US2019/028710, International Preliminary Report on Patentability dated Nov. 5, 2020", 7 pgs.
"Australian Application Serial No. 2019253572, First Examination Report dated Apr. 21, 21", 3 pgs.
"Australian Application Serial No. 2019257675, First Examination Report dated Jun. 8, 21", 3 pgs.
"Australian Application Serial No. 2019257675, Response filed Jun. 17, 21 to First Examination Report dated Jun. 8, 21", 17 pgs.
Wolterink, Jelmer M, et al., "Deep MR to CT Synthesis Using Unpaired Data", International Conference On Computer Analysis of Images and Patterns. CAIP 2017: Computer Analysis of Images and Patterns; [Lecture Notes in Computer Science; Lect.Notes Computer], Springer, Berlin, Heidelberg, (Sep. 26, 2017), 14-23.

* cited by examiner

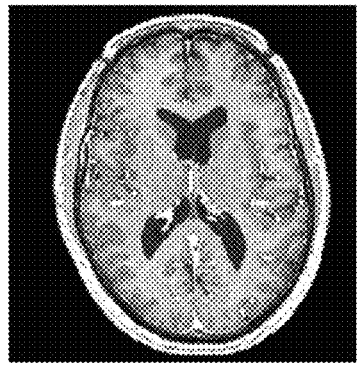
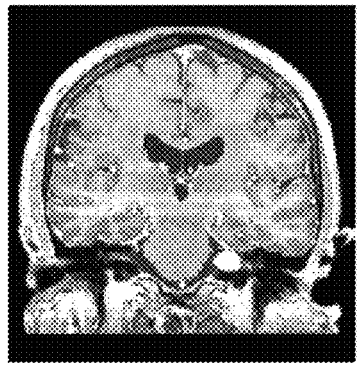
FIG. 9A　　　　　FIG. 9B　　　　　FIG. 9C
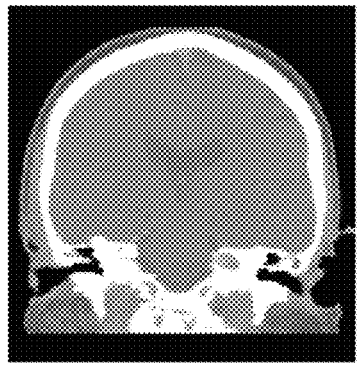
FIG. 10A　　　　　FIG. 10B　　　　　FIG. 10C
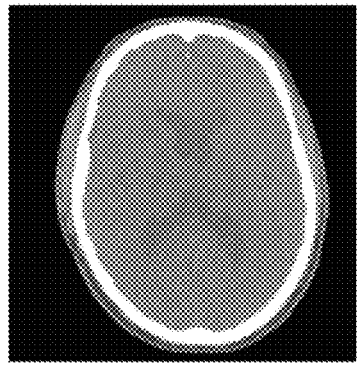
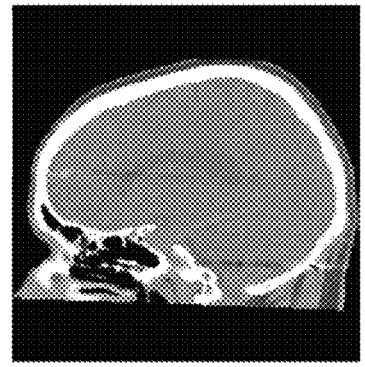
FIG. 11A　　　　　FIG. 11B　　　　　FIG. 11C

IMAGE SYNTHESIS USING ADVERSARIAL NETWORKS SUCH AS FOR RADIATION THERAPY

TECHNICAL FIELD

This document pertains generally, but not by way of limitation, to synthesis of medical images, and more particularly, to apparatus and techniques for automated (e.g., computer-implemented) translation of imaging data from a first imaging modality type (e.g., magnetic resonance (MR) imaging) to a different second imaging modality type (e.g., computed tomography (CT) imaging) at least in part using a statistical learning model, such as in support of radiation therapy delivery or radiation therapy treatment planning.

BACKGROUND

In radiotherapy or radiosurgery, treatment planning is generally performed using medical imaging of the patient. Analysis of such imaging generally involves delineation of target volumes and critical organs in the medical images. For example, segmentation or contouring of tumor and organs-at-risk (OARs) from patient images is generally considered a prerequisite for radiotherapy planning. Segmentation or other image processing might be performed on imaging data corresponding to a particular imaging modality type, such as computed tomography (CT) imaging. Use of semi-automated or automated segmentation techniques may rely on the input imaging data being CT imaging data. In some use cases, it may instead be desired to use magnetic resonance (MR) imaging primarily or exclusively as input imaging data for processing. Such MR imaging data may not be suitable for use with existing radiotherapy planning tools that rely on CT imaging, or for use with tools that rely on particular MR weighting approaches or MR imaging sequences that differ from the available input imaging data, for example. An image synthesis technique may be used to translate an image from a first modality type to a different, second modality type, such as to facilitate compatibility with radiation therapy treatment planning or therapy delivery tools.

In one approach, image translation may be performed using a machine learning technique trained using paired images. The phrase "paired images" may generally refer to use of different acquired images of the same patient to generate training data, where the different acquired images are obtained using different imaging modalities (e.g., CT vs. cone-beam imaging vs. conventional CT, T1-weighted MR vs. T2-weighted MR, as illustrative examples). Such an approach, relying upon paired imaging data, may present various challenges. For example, for training techniques to be effective, paired images may need to be perfectly or near-perfectly aligned in order to train a model that may faithfully synthesize an output image. Such alignment may be extremely difficult, if not impossible, to achieve because the images are usually acquired from different imaging devices or at different points in time, where the imaging subject has moved, such as from one scanner to another scanner. Such movement may create distortions or anatomical changes between imaging acquisitions. Registration techniques may be used to address such challenges in part, but such registration techniques also present their own challenges. Errors in registration will lead to degraded model performance due to imperfect training data.

OVERVIEW

As described herein, image synthesis generally involves receiving input imaging data and synthesizing output imaging data using a trained statistical learning model, where the output imaging data may then be used in downstream activities such as radiation therapy treatment planning or radiation therapy delivery. The present inventor has recognized, among other things, that a problem exists in applying statistical learning techniques, such as machine learning involving deep convolutional neural network (DCNN) techniques, for image synthesis (e.g., translation of images from a first imaging modality type to a different second imaging modality type), when unpaired images are to be used for training. The present inventor has developed, among other things, a statistical learning technique that does not rely upon paired imaging information in order to train a statistical learning model to perform image synthesis. In an example, a trained statistical learning model may include a convolutional neural network established as a generator convolutional network, and the generator may be trained at least in part using a separate convolutional neural network established as a discriminator convolutional network. The generator convolutional network and the discriminator convolutional network may form an adversarial network architecture wherein the discriminator convolutional network is adjusted during training to enhance or maximize a value of an objective over a distribution of inputs to the discriminator convolutional network, and the generator convolutional network to reduce or minimize the value of the objective over a distribution of inputs to the generator convolutional network.

By contrast with other approaches, the present inventor has also recognized, among other things, that the approaches described herein need not include training of two separate generator convolutional networks contemporaneously along with two separate discriminator convolutional networks, for use with unpaired imaging data. In this manner, the approaches described herein may provide significant savings in processing time and memory consumption (e.g., a factor of about 2× savings compared to other approaches involving two generator networks and two discriminator networks).

In an example, a computer-implemented method may be used for synthesizing a medical image using a trained statistical learning model, the method including receiving medical imaging data obtained using a first imaging modality type, applying the trained statistical learning model to the received medical imaging data to synthesize a medical image corresponding to a different second imaging modality type, and providing the synthesized medical image for presentation or for use in further processing. The trained statistical learning model may be established at least in part using a similarity determination between training imaging data provided at the model input, the training imaging data corresponding to the first imaging modality type and synthesized imaging data at the model output corresponding to the second imaging modality type, and the trained statistical learning model may be established at least in part using a separate statistical learning model, the separate statistical learning model established to discriminate between actual imaging data corresponding to the second imaging modality and the synthesized imaging data.

In an example, a computer-implemented method may include establishing a trained statistical learning model for synthesizing a medical image without requiring paired imaging for training, where the method comprises receiving training medical imaging data corresponding to a first imaging modality type, applying a statistical learning model to the received medical imaging data to synthesize imaging data corresponding to a different second imaging modality type, adjusting the statistical learning model at least in part using a similarity determination between the training imaging data and synthesized imaging data at the model output, and adjusting the statistical learning model at least in part using a separate statistical learning model, the separate statistical learning model established to discriminate between the synthesized imaging data and actual imaging data corresponding to the second imaging modality type.

In an example, a system for performing various computer-implemented techniques may include processing circuitry comprising at least one processor, and a storage medium comprising instructions, which when executed by the at least one processor, cause the processor to receive medical imaging data obtained using a first imaging modality type, apply the trained statistical learning model to the received medical imaging data to synthesize a medical image corresponding to a different second imaging modality type, and provide the synthesized medical image for presentation or for use in further processing. The trained statistical learning model may be established at least in part using a similarity determination between training imaging data provided at the model input, the training imaging data corresponding to the first imaging modality type and synthesized imaging data at the model output corresponding to the second imaging modality type, and the trained statistical learning model may be established at least in part using a separate statistical learning model, the separate statistical learning model established to discriminate between the synthesized imaging data and actual imaging data corresponding to the second imaging modality type.

This summary is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 9A, FIG. 9B, and FIG. 9C show illustrative examples comprising views of imaging data corresponding to a first imaging modality type.

FIG. 10A, FIG. 10B, and FIG. 10C show illustrative examples comprising views of synthesized imaging data corresponding to a second imaging modality type, the synthesized imaging data provided using a statistical learning model applied to the imaging data of FIG. 9A, FIG. 9B, and FIG. 9C, respectively.

FIG. 11A, FIG. 11B, and FIG. 11C show illustrative examples comprising views of actual imaging data obtained using the second imaging modality type, presented herein for comparison with the synthesized imaging data of FIG. 10A, FIG. 10B, and FIG. 10C, respectively.

DETAILED DESCRIPTION

As mentioned above, image translation from one imaging modality type to another may be performed in an automated (e.g., computer-implemented manner) such as using a trained statistical learning model to synthesize an output image. Such cross-modality image synthesis has many applications in radiation therapy. For example, it may be desired to generate a CT-like image (e.g., referred to as a "pseudo-CT" image or a "synthetic" CT image) based on an MR image to facilitate treatment planning using acquired MR imaging data. In another example, a higher-quality CT-like image may be synthesized (e.g., having less noise, less artifacts, having a higher resolution) from a comparatively lower-quality CT or cone-beam CT (CBCT) image as an input. In this latter example, synthesis offers a way to improve the image quality of comparatively lower-quality images (the lower-quality input imaging data may arise from imaging constraints such as lowering an imaging dose or using a shorter imaging duration to improve imaging speed or decrease latency).

As another example, MR imaging may involve use of many different sequences that may lead to highly variable image appearance, e.g., T1-weighted, T2-weighted, or FLAIR sequences, as illustrative examples. Use of different MR imaging sequences may present challenges when such images are provided as inputs to off-the-shelf imaging registration or imaging segmentation routines. The present inventor has recognized, that an output image may be synthesized to provide imaging data compatible with the registration or segmentation routine. For example, T2-weighted imaging data may be provided, representing a first imaging modality type, and from the T2-weighted imaging data, T1-weighted imaging data may be synthesized using a trained statistical learning model. One or more of registration or segmentation may then be performed on the synthesized imaging data.

Deep learning techniques, including deep convolutional neural networks (DCNNs), may be used for challenging medical imaging analysis problems, such as tumor detection, disease classification, or structure segmentation, as illustrative examples. A property that contributes to the success of DCNNs is an ability for such DCNNs to discern or "learn" a complex model directly from raw input data, without relying on hand-crafted features. Generally, the techniques described herein may be used to provide DCNN-facilitated image synthesis, such as to receive input imaging data obtained using a first image modality type, and to provide a synthesized output comprising output imaging data corresponding to a different second imaging modality.

Figure 1:
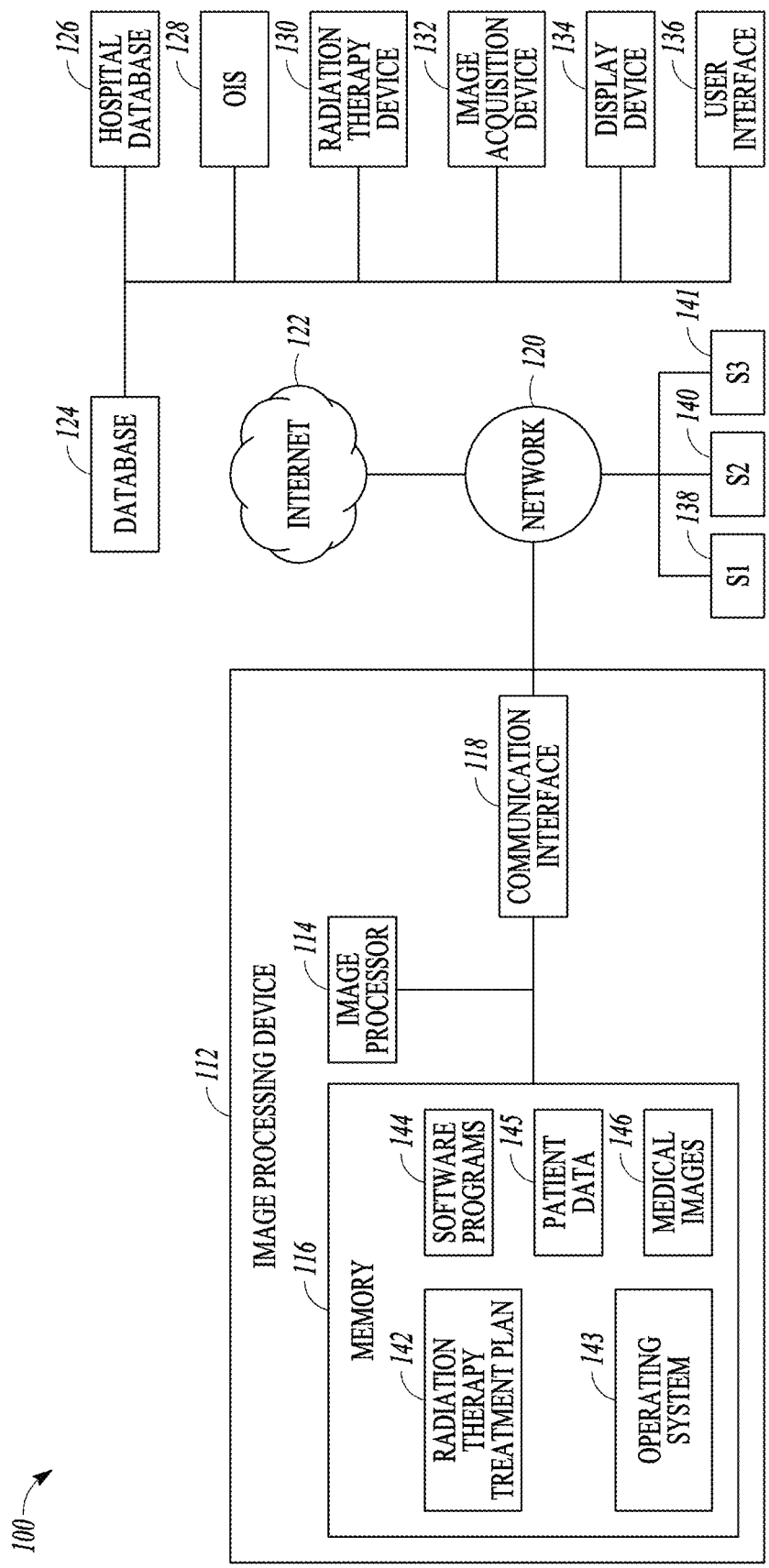
FIG. 1 illustrates an example comprising a radiotherapy system, such as for providing radiation therapy to a patient.

FIG. 1 illustrates an example comprising a radiotherapy system 100, such as for providing radiation therapy to a patient. The radiotherapy system 100 includes an image processing device 112. The image processing device 112 may be connected to a network 120. The network 120 may be connected to the Internet 122. The network 120 may connect the image processing device 112 with one or more of a database 124, a hospital database 126, an oncology information system (OIS) 128, a radiation therapy device 130, an image acquisition device 132, a display device 134, and a user interface 136. The image processing device 112 may be configured to generate radiation therapy treatment plans 142 to be used by the radiation therapy device 130.

The image processing device 112 may include a memory device 116, a processor 114 and a communication interface 118. The memory device 116 may store computer-executable instructions, such as an operating system 143, a radiation therapy treatment plans 142 (e.g., original treatment plans, adapted treatment plans and the like), software programs 144 (e.g., artificial intelligence, deep learning, neural networks, radiotherapy treatment plan software), and any other computer-executable instructions to be executed by the processor 114, such as corresponding to or using one or more techniques as shown and described elsewhere herein. In one embodiment, the software programs 144 may convert medical images of one format (e.g., MRI) to another format (e.g., CT) by producing synthetic images, such as a pseudo-CT image. For instance, the software programs 144 may include image processing programs to train a statistical learning model to convert a medical image 146 corresponding to one modality (e.g., an MRI image) into a synthetic image corresponding to a different modality (e.g., a CT image); alternatively, a statistical learning model may convert a CT image into an MRI image.

Illustrative examples are described elsewhere herein, such as below, for performing such image synthesis using a statistical learning model. In another embodiment, the software programs 144 may register the patient image (e.g., a CT image or an MR image) with that patient's dose distribution (also represented as an image) so that corresponding image voxels and dose voxels are associated appropriately by the network. In yet another embodiment, the software programs 144 may substitute functions of the patient images such as signed distance functions or processed versions of the images that emphasize some aspect of the image information. Such functions might emphasize edges or differences in voxel textures, or any other structural aspect useful to neural network learning. In another embodiment, the software programs 144 may substitute functions of the dose distribution that emphasize some aspect of the dose information. Such functions might emphasize steep gradients around the target, or any other structural aspect useful to neural network learning. The memory device 116 may store data, including medical images 146, patient data 145, and other data required to create and implement a radiation therapy treatment plan 142.

In addition to the memory 116 storing the software programs 144, it is contemplated that software programs 144 may be stored on a removable computer medium, such as a hard drive, a computer disk, a CD-ROM, a DVD, a HD, a Blu-Ray DVD, USB flash drive, a SD card, a memory stick, or any other suitable medium; and the software programs 144 when downloaded to image processing device 112 may be executed by image processor 114.

The processor 114 may be communicatively coupled to the memory device 116, and the processor 114 may be configured to execute computer executable instructions stored thereon. The processor 114 may send or receive medical images 146 to memory 116. For example, the processor 114 may receive medical images 146 from the image acquisition device 132 via the communication interface 118 and network 120 to be stored in memory 116. The processor 114 may also send medical images 146 stored in memory 116 via the communication interface 118 to the network 120 be either stored in database 124 or the hospital database 126.

Further, the processor 114 may utilize software programs 144 (e.g., a treatment planning software) along with the medical images 146 and patient data 145 to create the radiation therapy treatment plan 142. Medical images 146 may include information such as imaging data associated with a patient anatomical region, organ, or volume of interest segmentation data. Patient data 145 may include information such as (1) functional organ modeling data (e.g., serial versus parallel organs, appropriate dose response models, etc.); (2) radiation dosage data (e.g., dose-volume histogram (DVH) information; or (3) other clinical information about the patient and course of treatment (e.g., other surgeries, chemotherapy, previous radiotherapy, etc.).

In addition, the processor 114 may utilize software programs to generate intermediate data such as updated parameters to be used, for example, by a neural network model; or generate intermediate 2D or 3D images, which may then subsequently be stored in memory 116. The processor 114 may transmit an executable radiation therapy treatment plan 142 via the communication interface 118 to the network 120 to the radiation therapy device 130, where the radiation therapy plan will be used to treat a patient with radiation. In addition, the processor 114 may execute software programs 144 to implement functions such as image conversion, image segmentation, deep learning, neural networks, and artificial intelligence. For instance, the processor 114 may execute software programs 144 that train or contour a medical image; such software 144 when executed may train a boundary detector, or utilize a shape dictionary.

The processor 114 may be a processing device, include one or more general-purpose processing devices such as a microprocessor, a central processing unit (CPU), a graphics processing unit (GPU), an accelerated processing unit (APU), or the like. More particularly, the processor 214 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processor 114 may also be implemented by one or more special-purpose processing devices such as an application specific integrated circuit (ASIC), a field programmable gate array (FPGA), a digital signal processor (DSP), a System on a Chip (SoC), or the like. As would be appreciated by those skilled in the art, in some embodiments, the processor 114 may be a special-purpose processor, rather than a general-purpose processor. The processor 114 may include one or more known processing devices, such as a microprocessor from the Pentium™, Core™, Xeon™, or Itanium® family manufactured by Intel™, the Turion™, Athlon™, Sempron™, Opteron™, FX™, Phenom™ family manufactured by AMD™, or any of various processors manufactured by Sun Microsystems. The processor 114 may also include graphical processing units such as a GPU from the GeForce®, Quadro®, Tesla® family manufactured by Nvidia™, GMA, Iris™ family manufactured by Intel™ or the Radeon™ family manufactured by AMD™. The processor 114 may also include accelerated processing units such as the Xeon Phi™ family manufactured by Intel™. The disclosed embodiments are not limited to any type of processor(s) otherwise configured to meet the computing demands of identifying, analyzing, maintaining, generating, or providing large amounts of data or manipulating such data to perform the methods disclosed herein. In addition, the term "processor" may include more than one processor, for example, a multi-core design or a plurality of processors each having a multi-core design. The processor 114 may execute sequences of computer program instructions, stored in memory 116, to perform various operations, processes, methods that will be explained in greater detail below.

The memory device 116 may store medical images 146. In some embodiments, the medical images 146 may include one or more Mill image (e.g., 2D MRI, 3D MRI, 2D streaming MRI, 4D MRI, 4D volumetric MRI, 4D cine MRI, etc.), functional MRI images (e.g., fMRI, DCE-MRI, diffusion MRI), Computed Tomography (CT) images (e.g., 2D CT, Cone beam CT, 3D CT, 4D CT), ultrasound images (e.g., 2D ultrasound, 3D ultrasound, 4D ultrasound), Positron Emission Tomography (PET) images, X-ray images, fluoroscopic images, radiotherapy portal images, Single-Photo Emission Computed Tomography (SPECT) images, computer generated synthetic images (e.g., pseudo-CT images) and the like. Further, the medical images 146 may also include medical image data, for instance, training images, and ground truth images, contoured images, and dose images. In an embodiment, the medical images 146 may be received from the image acquisition device 132. Accordingly, image acquisition device 132 may include a MRI imaging device, a CT imaging device, a PET imaging device, an ultrasound imaging device, a fluoroscopic device, a SPECT imaging device, an integrated Linear Accelerator and MRI imaging device, or other medical imaging devices for obtaining the medical images of the patient. The medical images 146 may be received and stored in any type of data or any type of format that the image processing device 112 may use to perform operations consistent with the disclosed embodiments. The memory device 116 may be a non-transitory computer-readable medium, such as a read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a compact disc read-only memory (CD-ROM), a digital versatile disc (DVD) or other optical storage, a cassette tape, other magnetic storage device, or any other non-transitory medium that may be used to store information including image, data, or computer executable instructions (e.g., stored in any format) capable of being accessed by the processor 114, or any other type of computer device. The computer program instructions may be accessed by the processor 114, read from the ROM, or any other suitable memory location, and loaded into the RAM for execution by the processor 114. For example, the memory 116 may store one or more software applications. Software applications stored in the memory 116 may include, for example, an operating system 143 for common computer systems as well as for software-controlled devices. Further, the memory 116 may store an entire software application, or only a part of a software application, that are executable by the processor 114. For example, the memory device 116 may store one or more radiation therapy treatment plans 142.

The image processing device 112 may communicate with the network 120 via the communication interface 118, which may be communicatively coupled to the processor 114 and the memory 116. The Communication interface 118 may provide communication connections between the image processing device 112 and radiotherapy system 100 components (e.g., permitting the exchange of data with external devices). For instance, the communication interface 118 may in some embodiments have appropriate interfacing circuitry to connect to the user interface 136, which may be a hardware keyboard, a keypad, or a touch screen through which a user may input information into radiotherapy system 100.

Communication interface 118 may include, for example, a network adaptor, a cable connector, a serial connector, a USB connector, a parallel connector, a high-speed data transmission adaptor (e.g., such as fiber, USB 3.0, Thunderbolt, and the like), a wireless network adaptor (e.g., such as a WiFi adaptor), a telecommunication adaptor (e.g., 3G, 4G/LTE and the like), and the like. Communication interface 118 may include one or more digital or analog communication devices that permit image processing device 112 to communicate with other machines and devices, such as remotely located components, via the network 120.

The network 120 may provide the functionality of a local area network (LAN), a wireless network, a cloud computing environment (e.g., software as a service, platform as a service, infrastructure as a service, etc.), a client-server, a wide area network (WAN), and the like. For example, network 120 may be a LAN or a WAN that may include other systems S1 (138), S2 (140), and S3 (141). Systems 51, S2, and S3 may be identical to image processing device 112 or may be different systems. In some embodiments, one or more of systems in network 120 may form a distributed computing/simulation environment that collaboratively performs the embodiments described herein. In some embodiments, one or more systems S1, S2, and S3 may include a CT scanner that obtains CT images (e.g., medical images 146). In addition, network 120 may be connected to internet 122 to communicate with servers and clients that reside remotely on the internet.

Therefore, network 120 may allow data transmission between the image processing device 112 and a number of various other systems and devices, such as the OIS 128, the radiation therapy device 130, and the image acquisition device 132. Further, data generated by the OIS 128 or the image acquisition device 132 may be stored in the memory 116, the database 124, or the hospital database 126. The data may be transmitted/received via network 120, through communication interface 118 in order to be accessed by the processor 114, as required.

The image processing device 112 may communicate with database 124 through network 120 to send/receive a plurality of various types of data stored on database 124. For example, database 124 may include machine data that is information associated with a radiation therapy device 130, image acquisition device 132, or other machines relevant to radiotherapy. Machine data information may include radiation beam size, arc placement, beam on and off time duration, machine parameters, segments, multi-leaf collimator (MLC) configuration, gantry speed, MRI pulse sequence, and the like. Database 124 may be a storage device and may be equipped with appropriate database administration software programs. One skilled in the art would appreciate that database 124 may include a plurality of devices located either in a central or a distributed manner.

In some embodiments, database 124 may include a processor-readable storage medium (not shown). While the processor-readable storage medium in an embodiment may be a single medium, the term "processor-readable storage medium" should be taken to include a single medium or multiple media (e.g., a centralized or distributed database, or associated caches and servers) that store the one or more sets of computer executable instructions or data. The term "processor-readable storage medium" shall also be taken to include any medium that is capable of storing or encoding a set of instructions for execution by a processor and that cause the processor to perform any one or more of the methodologies of the present disclosure. The term "processor readable storage medium" shall accordingly be taken to include, but not be limited to, solid-state memories, optical and magnetic media. For example, the processor readable storage medium may be or may include one or more volatile, non-transitory, or non-volatile tangible computer-readable media.

Image processor 114 may communicate with database 124 to read images into memory 116 or store images from memory 116 to database 124. For example, the database 124 may be configured to store a plurality of images (e.g., 3D MRI, 4D MRI, 2D MRI slice images, CT images, 2D Fluoroscopy images, X-ray images, raw data from MR scans or CT scans, Digital Imaging and Communications in Medicine (DIMCOM) data, etc.) that the database 124 received from image acquisition device 132. Database 124 may store data to be used by the image processor 114 when executing software program 144, or when creating radiation therapy treatment plans 142. Database 124 may store the data produced by the trained neural network including the network parameters constituting the model learned by the network and the resulting predicted data. The image processing device 112 may receive the imaging data 146 (e.g., 2D MRI slice images, CT images, 2D Fluoroscopy images, X-ray images, 3D MRI images, 4D MRI images, etc.) either from the database 124, the radiation therapy device 130 (e.g., a MRI-Linac), and or the image acquisition device 132 to generate a treatment plan 142.

In an embodiment, the radiotherapy system 100 may include an image acquisition device 132 that may acquire medical images (e.g., Magnetic Resonance Imaging (MRI) images, 3D MRI, 2D streaming MRI, 4D volumetric MRI, Computed Tomography (CT) images, Cone-Beam CT, Positron Emission Tomography (PET) images, functional MRI images (e.g., fMRI, DCE-MRI and diffusion MRI), X-ray images, fluoroscopic image, ultrasound images, radiotherapy portal images, single-photo emission computed tomography (SPECT) images, and the like) of the patient. Image acquisition device 132 may, for example, be an MRI imaging device, a CT imaging device, a PET imaging device, an ultrasound device, a fluoroscopic device, a SPECT imaging device, or any other suitable medical imaging device for obtaining one or more medical images of the patient. Images acquired by the imaging acquisition device 132 may be stored within database 124 as either imaging data or test data. By way of example, the images acquired by the imaging acquisition device 132 may be also stored by the image processing device 112, as medical image data 146 in memory 116.

In an embodiment, for example, the image acquisition device 132 may be integrated with the radiation therapy device 130 as a single apparatus (e.g., a MRI device combined with a linear accelerator, also referred to as an "MRI-Linac." Such an MRI-Linac may be used, for example, to determine a location of a target organ or a target tumor in the patient, so as to direct radiation therapy accurately according to the radiation therapy treatment plan 142 to a predetermined target.

The image acquisition device 132 may be configured to acquire one or more images of the patient's anatomy for a region of interest (e.g., a target organ, a target tumor or both). Each image, typically a 2D image or slice, may include one or more parameters (e.g., a 2D slice thickness, an orientation, and a location, etc.). In an embodiment, image acquisition device 132 may acquire a 2D slice in any orientation. For example, an orientation of the 2D slice may include a sagittal orientation, a coronal orientation, or an axial orientation. The processor 114 may adjust one or more parameters, such as the thickness or orientation of the 2D slice, to include the target organ or target tumor. In an embodiment, 2D slices may be determined from information such as a 3D MRI volume. Such 2D slices may be acquired by the image acquisition device 132 in "near real-time" while a patient is undergoing radiation therapy treatment, for example, when using the radiation therapy device 130. "Near real-time" meaning acquiring the data in milliseconds or less duration.

The image processing device 112 may generate and store radiation therapy treatment plans 142 for one or more patients. The radiation therapy treatment plans 142 may provide information about a particular radiation dose to be applied to each patient. The radiation therapy treatment plans 142 may also include other radiotherapy information, such as beam angles, dose-histogram-volume information, the number of radiation beams to be used during therapy, the dose per beam, and the like.

The image processor 114 may generate the radiation therapy treatment plan 142 by using software programs 144 such as treatment planning software, such as Monaco®, manufactured by Elekta AB of Stockholm, Sweden. In order to generate the radiation therapy treatment plans 242, the image processor 114 may communicate with the image acquisition device 132 (e.g., a CT device, a MRI device, a PET device, an X-ray device, an ultrasound device, etc.) to access images of the patient and to delineate a target, such as a tumor. In some embodiments, the delineation of one or more organs at risk (OARs), such as healthy tissue surrounding the tumor or in close proximity to the tumor may be required. Therefore, segmentation of the OAR may be performed when the OAR is close to the target tumor. In addition, if the target tumor is close to the OAR (e.g., prostate in near proximity to the bladder and rectum), then by segmenting the OAR from the tumor, the radiotherapy system 100 may study the dose distribution not only in the target, but also in the OAR.

In order to delineate a target organ or a target tumor from the OAR, medical images, such as MRI images, CT images, PET images, fMRI images, X-ray images, ultrasound images, radiotherapy portal images, SPECT images and the like, of the patient undergoing radiotherapy may be obtained non-invasively by the image acquisition device 132 to reveal the internal structure of a body part. Based on the information from the medical images, a 3D structure of the relevant anatomical portion may be obtained. In addition, during a treatment planning process, many parameters may be taken into consideration to achieve a balance between efficient treatment of the target tumor (e.g., such that the target tumor receives enough radiation dose for an effective therapy) and low irradiation of the OAR(s) (e.g., the OAR(s) receives as low a radiation dose as possible). Other parameters that may be considered include the location of the target organ and the target tumor, the location of the OAR, and the movement of the target in relation to the OAR. For example, the 3D structure may be obtained by contouring the target or contouring the OAR within each 2D layer or slice of an MRI or CT image and combining the contour of each 2D layer or slice. The contour may be generated manually (e.g., by a physician, dosimetrist, or health care worker using a program such as MONACO™ manufactured by Elekta AB of Stockholm, Sweden) or automatically (e.g., using a program such as the Atlas-based auto-segmentation software, ABAS™, manufactured by Elekta AB of Stockholm, Sweden). In certain embodiments, the 3D structure of a target tumor or an OAR may be generated automatically by the treatment planning software, such as using one or more techniques as shown and described elsewhere herein.

After the target tumor and the OAR(s) have been located and delineated, a dosimetrist, physician or healthcare worker may determine a dose of radiation to be applied to the target tumor, as well as any maximum amounts of dose that may be received by the OAR proximate to the tumor (e.g., left and right parotid, optic nerves, eyes, lens, inner ears, spinal cord, brain stem, and the like). After the radiation dose is determined for each anatomical structure (e.g., target tumor, OAR), a process known as inverse planning may be performed to determine one or more treatment plan parameters that would achieve the desired radiation dose distribution. Examples of treatment plan parameters include volume delineation parameters (e.g., which define target volumes, contour sensitive structures, etc.), margins around the target tumor and OARs, beam angle selection, collimator settings, and beam-on times. During the inverse-planning process, the physician may define dose constraint parameters that set bounds on how much radiation an OAR may receive (e.g., defining full dose to the tumor target and zero dose to any OAR; defining 95% of dose to the target tumor; defining that the spinal cord, brain stem, and optic structures receive ≤45 Gy, ≤55 Gy and ≤54 Gy, respectively). The result of inverse planning may constitute a radiation therapy treatment plan 142 that may be stored in memory 116 or database 124. Some of these treatment parameters may be correlated. For example, tuning one parameter (e.g., weights for different objectives, such as increasing the dose to the target tumor) in an attempt to change the treatment plan may affect at least one other parameter, which in turn may result in the development of a different treatment plan. Thus, the image processing device 112 may generate a tailored radiation therapy treatment plan 142 having these parameters in order for the radiation therapy device 130 to provide radiotherapy treatment to the patient.

In addition, the radiotherapy system 100 may include a display device 134 and a user interface 136. The display device 134 may include one or more display screens that display medical images, interface information, treatment planning parameters (e.g., contours, dosages, beam angles, etc.) treatment plans, a target, localizing a target or tracking a target, or any related information to the user. The user interface 136 may be a keyboard, a keypad, a touch screen or any type of device that a user may input information to radiotherapy system 100. Alternatively, the display device 134 and the user interface 136 may be integrated into a device such as a tablet computer (e.g., Apple iPad®, Lenovo Thinkpad®, Samsung Galaxy®, etc.).

Furthermore, a subset or an entirety of the components of the radiotherapy system 100 may be implemented as a virtual machine (e.g., VMWare™, Hyper-V™, and the like). For instance, a virtual machine may be software that functions as hardware. Therefore, a virtual machine may include at least one or more virtual processors, one or more virtual memories, and one or more virtual communication interfaces that together function as hardware. For example, the image processing device 112, the OIS 128, the image acquisition device 132 could be implemented as a virtual machine. Given the processing power, memory, and computational capability available, the entire radiotherapy system 100 could be implemented as a virtual machine.

Figure 2:
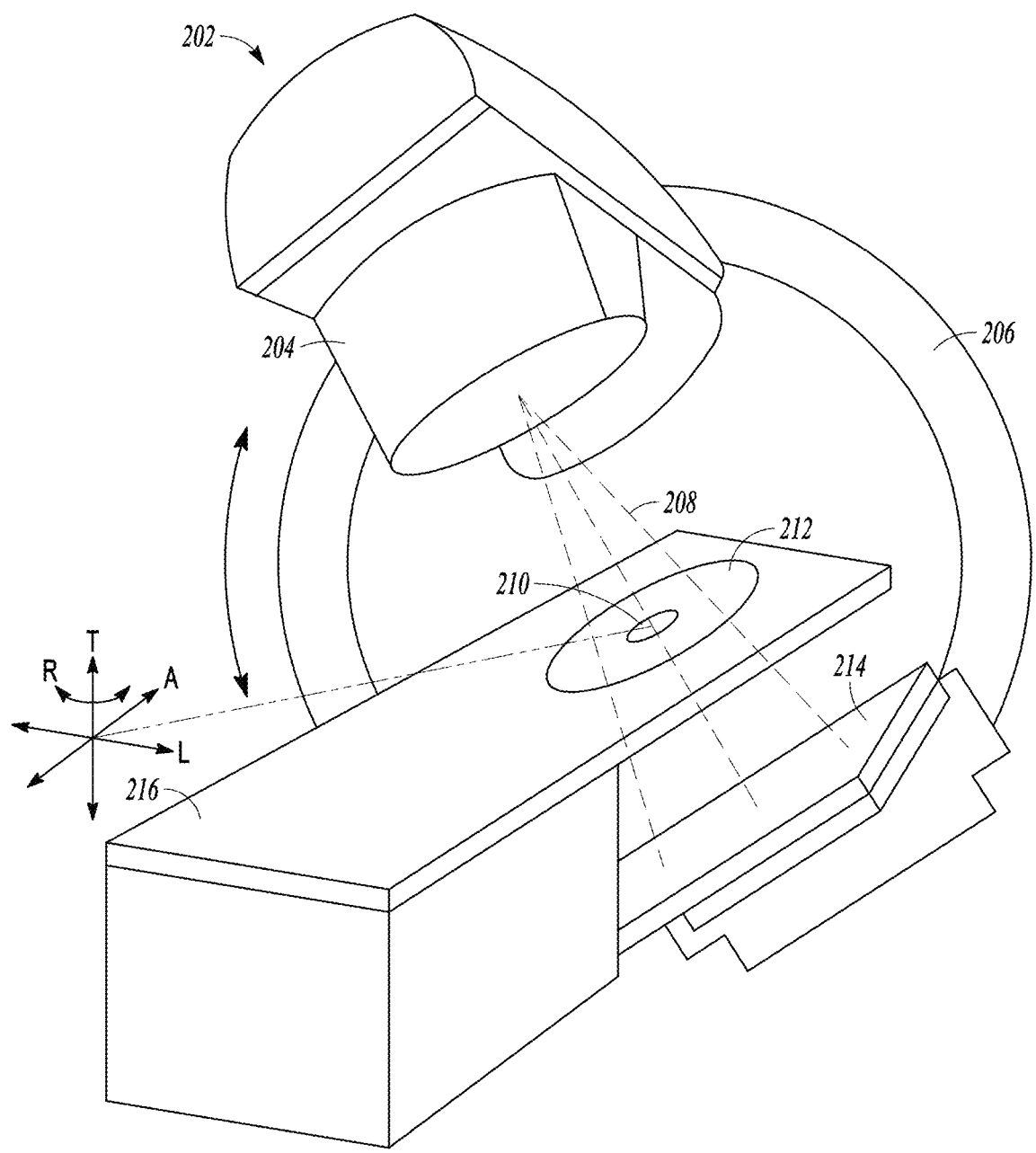
FIG. 2 illustrates an example including a radiation therapy device that may include a radiation source, such as an X-ray source or a linear accelerator, a couch, an imaging detector, and a radiation therapy output.

FIG. 2 illustrates an example including a radiation therapy device 202 that may include a radiation source, such as an X-ray source or a linear accelerator, a couch 216, an imaging detector 214, and a radiation therapy output 204. The radiation therapy device 202 may be configured to emit a radiation beam 208 to provide therapy to a patient. The radiation therapy output 204 may include one or more attenuators or collimators, such as a multi-leaf collimator (MLC). A patient may be positioned in a region 212, supported by the treatment couch 216 to receive a radiation therapy dose according to a radiation therapy treatment plan.

The radiation therapy output 204 may be mounted or attached to a gantry 206 or other mechanical support. One or more chassis motors (not shown) may rotate the gantry 206 and the radiation therapy output 204 around couch 216 when the couch 216 is inserted into the treatment area. In an embodiment, gantry 206 may be continuously rotatable around couch 216 when the couch 216 is inserted into the treatment area. In another embodiment, gantry 206 may rotate to a predetermined position when the couch 216 is inserted into the treatment area. For example, the gantry 206 may be configured to rotate the therapy output 204 around an axis ("A"). Both the couch 216 and the radiation therapy output 204 may be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch 216 movements or rotations in order to properly position the patient in or out of the radiation beam 208 according to a radiation therapy treatment plan. For example, both the couch 216 and the gantry 206 may be independently moveable with respect to each other in multiple degrees of freedom, allowing the patient to be positioned such that the radiation beam 208 precisely may target the tumor.

The coordinate system (including axes A, T, and L) shown in FIG. 2 may have an origin located at an isocenter 210. The isocenter may be defined as a location where the central axis of the radiation therapy beam 208 intersects the origin of a coordinate axis, such as to deliver a prescribed radiation dose to a location on or within a patient. Alternatively, the isocenter 210 may be defined as a location where the central axis of the radiation therapy beam 208 intersects the patient for various rotational positions of the radiation therapy output 204 as positioned by the gantry 206 around the axis A.

Gantry 206 may also have an attached imaging detector 214. The imaging detector 214 preferably located opposite to the radiation source 204, and in an embodiment, the imaging detector 214 may be located within a field of the therapy beam 208. The imaging detector 214 may be mounted on the gantry 206 preferably opposite the radiation therapy output 204, such as to maintain alignment with the therapy beam 208. The imaging detector 214 rotating about the rotational axis as the gantry 206 rotates. In an embodiment, the imaging detector 214 may be a flat panel detector (e.g., a direct detector or a scintillator detector). In this manner, the imaging detector 214 may be used to monitor the therapy beam 208 or the imaging detector 214 may be used for imaging the patient's anatomy, such as portal imaging. The control circuitry of radiotherapy device 202 may be integrated within system 100 or remote from it.

In an illustrative embodiment, one or more of the couch 216, the therapy output 204, or the gantry 206 may be automatically positioned, and the therapy output 204 may establish the therapy beam 208 according to a specified dose for a particular therapy delivery instance. A sequence of therapy deliveries may be specified according to a radiation therapy treatment plan, such as using one or more different orientations or locations of the gantry 206, couch 216, or therapy output 204. The therapy deliveries may occur sequentially, but may intersect in a desired therapy locus on or within the patient, such as at the isocenter 210. A prescribed cumulative dose of radiation therapy may thereby be delivered to the therapy locus while damage to tissue nearby the therapy locus may be reduced or avoided.

The example of FIG. 2 generally illustrates an embodiment of a radiation therapy device configured to provide radiotherapy treatment to a patient, including a configuration where a radiation therapy output may be rotated around a central axis (e.g., an axis "A"). Other radiation therapy output configurations may be used. For example, a radiation therapy output may be mounted to a robotic arm or manipulator having multiple degrees of freedom. In yet another embodiment, the therapy output may be fixed, such as located in a region laterally separated from the patient, and a platform supporting the patient may be used to align a radiation therapy isocenter with a specified target locus within the patient. In another embodiment, a radiation therapy device may be a combination of a linear accelerator and an image acquisition device. In some embodiments, the image acquisition device may be an MRI, an X-ray, a CT, a CBCT, a spiral CT, a PET, a SPECT, an optical tomography, a fluorescence imaging, ultrasound imaging, or radiotherapy portal imaging device, etc., as would be recognized by one of ordinary skill in the art.

Figure 3:
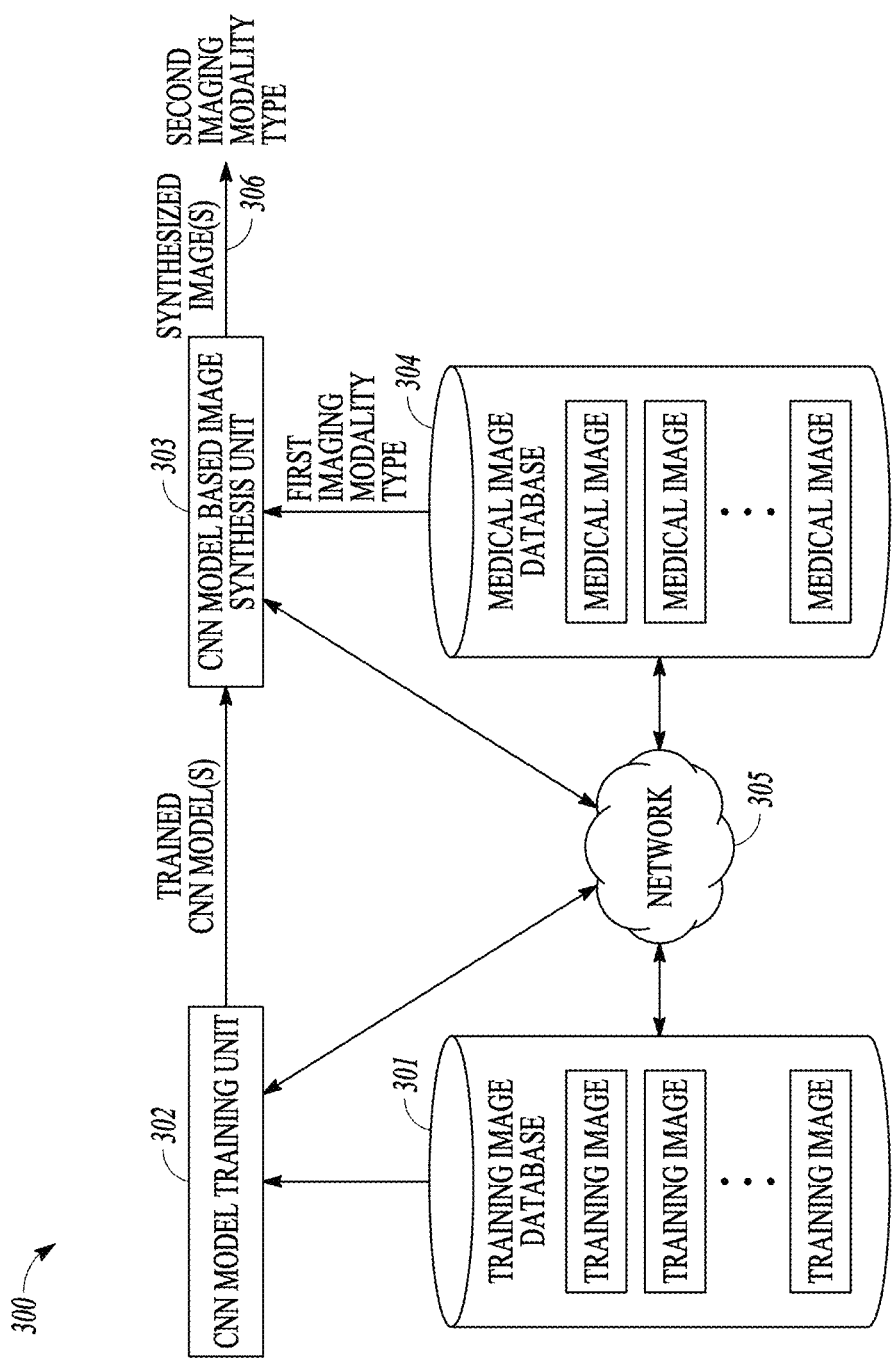
FIG. 3 illustrates an example including an architecture for performing training of at least one statistical learning model (e.g., a convolutional neural network (CNN)) and for providing synthesized images using a CNN model-based image synthesis technique.

FIG. 3 illustrates an example including a system 300 architecture for performing training of at least one statistical learning model (e.g., a convolutional neural network (CNN)) and for providing synthesized images using a CNN model-based image synthesis technique. The system 300 may be included as a portion of the radiotherapy system 100 as shown in FIG. 1, or the system 300 of FIG. 3 may be communicatively coupled to such a radiotherapy system. As shown in FIG. 3, the system 300 may include components for performing two stages, a training stage and an image synthesis stage. To perform the training stage, the system 300 may include a training image database 301 and a CNN model training unit 302. To perform synthesis, the system 300 may include a CNN model-based image synthesis unit 303 and a medical image database 304. In some embodiments, the system 300 may include more or less of the components shown in FIG. 3. For example, when a CNN model for image synthesis is pre-trained and provided, the system 300 may only include the CNN model-based image synthesis unit 303 and the medical image database 304. The system 300 may optionally include a network 305. In some embodiments, the network 305 may be replaced by wired data communication systems or devices.

In some embodiments, the various components of the system 300 may be located remotely from each other or in different spaces, and be connected through the network 305 as shown in FIG. 3. In some embodiments, certain components of the system 300 may be located on the same site or inside one device. For example, the training image database 301 may be located on site with the CNN model training unit 302, or be part of the CNN model training unit 302. As another example, the CNN model training unit 302 and the image synthesis unit 303 may be inside the same computer or processing device.

As shown in FIG. 3, the CNN model training unit 302 may communicate with the training image database 301 to receive one or more sets of training images. The sets of training images stored in the training image database 301 may be obtained from a medical image database, for example, a medical image database containing previously acquired medical images during radiotherapy treatment sessions. The set of training images may include 3D imaging data, or 2D imaging data. 3D imaging data may be selectively divided to one or more sequential stacks of adjacent 2D images. A count of adjacent 2D images in each stack may be determined based on various factors, such as the size of the 3D image, a specific framework of the CNN model, the relationship between the anatomical structures in the adjacent 2D images along an axis orthogonal to the 2D image, or in view of other factors.

Consistent with the disclosed embodiments, the training images may be acquired using various imaging modalities, including MRI, functional MRI (e.g., fMRI, DCE-MRI and diffusion MRI), CT, CBCT, Spiral CT, PET, SPECT, X-ray, optical tomography, fluorescence imaging, ultrasound imaging, and radiotherapy portal imaging, etc. In some embodiments, the training data may be collected from an Oncology Information System or other centralized repository. For example, the training images may be acquired by the image acquisition device 232 of FIG. 1.

Referring back to FIG. 3, the CNN model training unit 302 may use the training images received from training image database 301 to train a CNN model to receive imaging data corresponding to a first imaging modality type and to synthesize imaging data corresponding to a different, second imaging modality type. For example, a training architecture may include aspects shown in FIG. 4 (corresponding to an adversarial training architecture). The CNN model training unit 302 may include a processor and a non-transitory computer-readable medium. The processor may conduct the training by performing instructions of a training process stored in the computer-readable medium. The CNN model training unit 302 may additionally include input and output interfaces to communicate with the training image database 301, network 305, or a user interface (not shown). The user interface may be used for selecting sets of training images, adjusting one or more parameters of the training process, or for selecting or modifying a framework of a CNN model, as illustrative examples. The CNN model training unit 302 may be implemented with hardware specially programmed by software that performs the training process.

The image synthesis unit 303 may receive at least one trained CNN model from the CNN model training unit 302. The image synthesis unit 303 may include a processor and a non-transitory computer-readable medium (as mentioned in relation to the system 100 of FIG. 1). The processor may conduct synthesis of imaging information according to instructions stored in the medium. The image synthesis unit 303 may additionally include input and output interfaces to communicate with the medical image database 304, the network 305, or a user interface. The user interface may be used for selecting imaging information to be translated from a first imaging modality type to a second imaging modality type, including initiating an image synthesis process, displaying the input or output images, or performing further analysis based on the input imaging data or synthesized output imaging data. Various techniques for performing CNN-based image synthesis are described in relation to the examples elsewhere herein, such as shown and described in relation to FIG. 4, FIG. 5, FIG. 6, FIG. 7, or FIG. 8.

The image synthesis unit 303 may communicate with medical image database 304 to receive input imaging data for use in synthesis of different output imaging data. The images stored in medical image database 304 may be obtained from a medical image database, which contains 2D or 3D images of radiotherapy treatment sessions, for example. As described herein, image data may be reconstructed from 2D projection images acquired by medical imaging devices, such as image acquisition device 232 shown in FIG. 2. Referring back to FIG. 3, the image synthesis unit 303 may provide one or more synthesized images 306 for use in further processing, such as in support of radiation therapy treatment planning or radiotherapy delivery. In an example, an image 306 output by the image synthesis unit 303 may be stored within the training image database 401 or otherwise used, such as for further training a statistical learning model.

The imaging data to be translated using the image synthesis unit 303 may be acquired using various imaging modalities, including MRI, functional MRI (e.g., fMRI, DCE-MRI and diffusion MRI), CT, CBCT, Spiral CT, PET, SPECT, X-ray, optical tomography, fluorescence imaging, ultrasound imaging, and radiotherapy portal imaging, etc. In some embodiments, the medical image database 304 may be an integrated part of the image synthesis unit 303, or located on the same site of the image synthesis unit 303, such as in a radiotherapy treatment room. The network 305 may provide connections between any of the above described components in the system 300. For example, the network 305 may be a local area network (LAN), a wireless network, a cloud computing environment (e.g., software as a service, platform as a service, infrastructure as a service), a client-server, a wide area network (WAN), etc.

Figure 4:
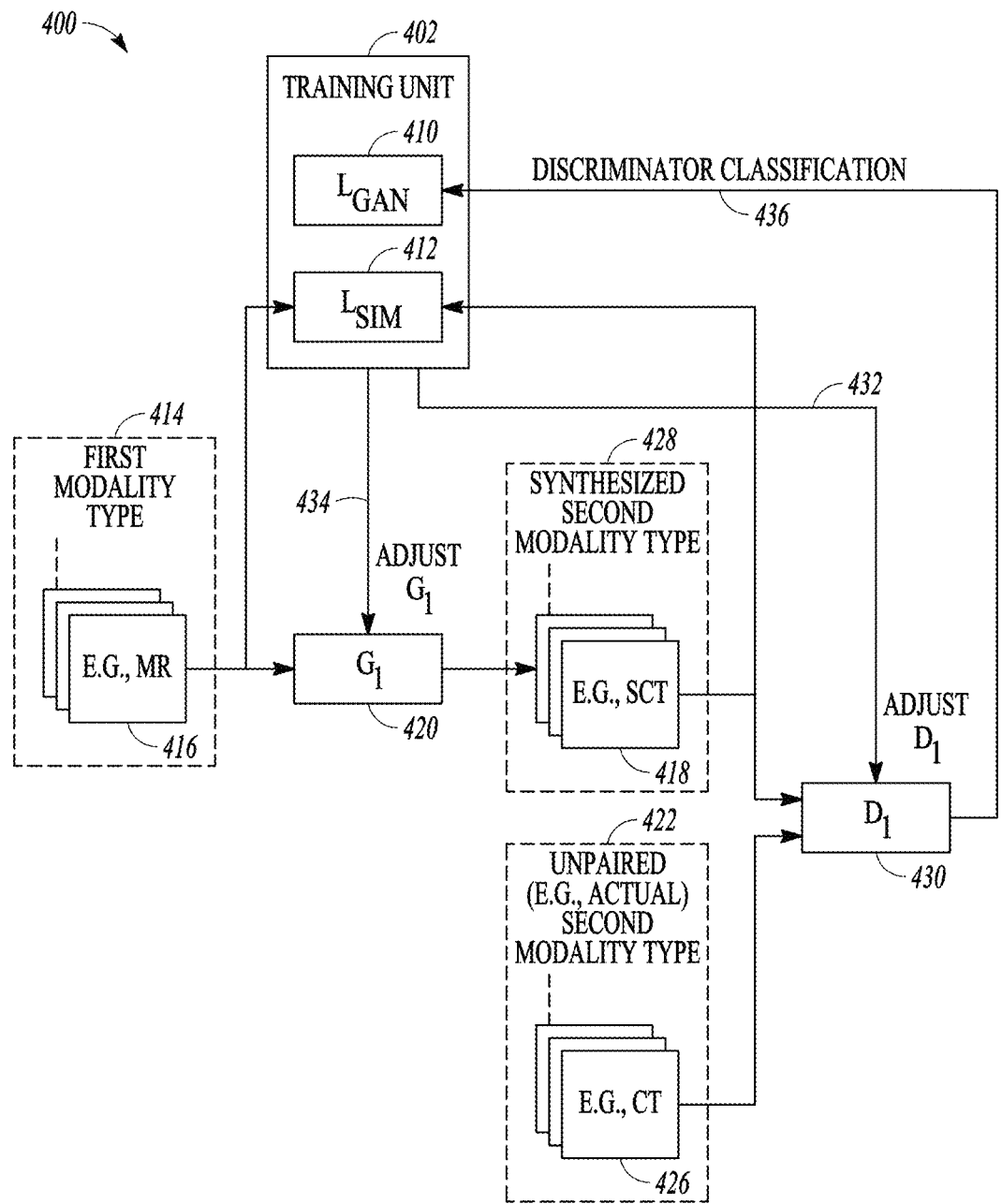
FIG. 4 illustrates an example including an adversarial training architecture for performing training of at least one statistical learning model (e.g., a convolutional neural network (CNN)), such as for providing synthesized images using a CNN model-based image synthesis technique.

FIG. 4 illustrates an example including an adversarial training architecture 400 for performing training of at least one statistical learning model (e.g., a generator convolutional neural network (CNN), "$G_1$" 420), such as for providing synthesized images 428 using a CNN model-based image synthesis technique. The training architecture 400 shown illustratively in FIG. 4 does not require use of "paired" imaging information. Input imaging data 414 used for training may include images (e.g., an image 416) corresponding to a first imaging modality type, such as MR imaging data. Unpaired imaging data 422 may also be used, such as corresponding to a different second imaging modality type, such as including images (e.g., an image 426) that need not be registered, or aligned with corresponding images in the input imaging data 414.

As mentioned elsewhere herein, a statistical learning model may be trained in a manner that does not rely on "paired" imaging data. "Paired" imaging data in a training context may refer to pairing of first imaging data corresponding to a first imaging modality type and related "paired" second imaging data corresponding to a different second imaging modality type. In a "paired" scheme, the second imaging data includes images that are aligned (e.g., registered) or otherwise obtained to correspond as closely as possible to respective images from the first imaging data. By contrast, use of "unpaired" imaging data does not require alignment or close correspondence between the training images used for the first imaging data and the different second imaging data. For example, the first imaging data may relate or otherwise correspond to a first set of patients whereas the second imaging data may relate or otherwise correspond to a partially different or entirely different set of patients.

Generally, unpaired imaging data are much simpler to obtain. As an illustrative example, many CT images and many MR images (e.g., hundreds or more) may be used for training if no requirement exists that each CT image has a well-aligned corresponding MR image or vice versa.

In the example of FIG. 4, the architecture 400 may include a single generator convolutional neural network (CNN) 420, "$G_1$," and a single discriminator convolutional neural network 430, "$D_1$." In the adversarial scheme shown for the architecture 400, the generator 420 is responsible to map or translate its input (e.g., image 416) from one domain (e.g., one modality type) to another modality type (e.g., to produce synthesized imaging data 428, such as an synthesized image 418). As an illustrative example, the input image 416 is an MR image, and the output image 418 is a "pseudo"-CT image or synthetic CT (SCT) image. The discriminator 430 facilitates training of the generator 420 by aiming to discriminate between synthesized imaging data 428 from the generator 420 as compared to unpaired training imaging data 422 representing actual or "real" CT imaging data (e.g., including a CT image 426 obtained using CT imaging rather than being synthesized).

The architecture 400 may be referred to as type of generative adversarial network (GAN), where the generator 420 and discriminator 430 are in competition, with the generator adjusted or otherwise optimized to provide synthetic imaging data 428 that corresponds as closely as possible to actual imaging data 422 to "fool" the discriminator 430. The discriminator 430 output 436 may be a classification value, such as a value between zero and one, with one representing a determination that an input image to the discriminator represents an actual image, and zero representing a determination that the input image is a "fake." In the limit, as training progresses, the generator 420 may produce imaging data 428 so closely resembling actual imaging data 422 that the discriminator 430 is unable to distinguish between the synthesized imaging data 428 and the actual imaging data 422 used for training. Once the training is complete (e.g., the generator 420 is adjusted to provide imaging data approaching a specified correlation with actual imaging data according to the discriminator 430), the generator 420 model may be saved and used separately for image synthesis.

Without sufficient constraints, the generator 420 model may create images that look real to the discriminator 430 but have very poor correlation with the generator 420 model input. As an illustrative example, in the worst case, the generator 420 may always produce a fixed output image with no dependence on the input image. In another illustrative example, the generator 420 may randomly output a real CT image from the corpus of training imaging data 422.

Because the approach shown in FIG. 4 does not rely on paired training data, an output of the generator 420 is not compared directly with some corresponding ground truth. Instead, a cross-modality similarity measure 412 may be used, such as implementing a similarity determination that directly compares synthesized imaging data 428 from the output of the generator 420 with imaging data 414 at the generator 420 input. This avoids a mode-collapsing problem and helps to make sure that the generator 420 produces synthesized imaging data 428 that is well-correlated with respect to the generator 420 input imaging data 414. The training architecture 400 shown in FIG. 4 may be partially or entirely computer-implemented, such as including use of a training unit 402.

A representation of an optimization approach implemented by the training unit 402 may be expressed as follows:

$$G^* = \underset{G}{\operatorname{argmin}}\ \underset{D}{\operatorname{max}} L(G, D) \qquad \text{EQN. 1}$$

In EQN. 1, G* represents a generator 420 having adjusted (e.g., optimized) parameters such as provided by an output 434 of the training unit 402, and "L(G,D)" represents a "loss" function or objective function, "L". The approach shown by EQN. 1 can refer to adjusting the discriminator 430 convolutional network to enhance or maximize a value of the objective over a distribution of inputs to the discriminator 430, and adjusting the generator 420 to reduce or minimize the value of the objective over a distribution of inputs to generator 420. Various approaches may be used to implement such training, such as including performing a stochastic gradient descent (SGD) iteration to adjust the generator 420 using the output 434, then performing a stochastic gradient descent iteration to adjust the discriminator 430 using output 432, and so on. Such adjustment may include modifying parameters within respective deep convolutional neural networks defining the generator 420 and the discriminator 430, respectively. Other training techniques may be used, such as SGD with momentum, a Nesterov accelerated gradient technique, AdaGrad, Adadelta, RMSprop, or Adam. Other techniques can be used such as involving evolutionary methods, genetic techniques, simulated annealing, or particle swarm optimization, as illustrative examples. As an illustrative example, the discriminator 430 may be implemented using a convolutional neural network acting as a classifier, such as shown illustratively in the example of FIG. 5. The generator 420 may be implemented using a convolutional neural network having an architecture as shown in FIG. 6, such as including short-range or long-range skip connections between convolutional layers. Referring back to FIG. 4, the objective function may include contributions corresponding to the adversarial objective 410, such represented by "$L_{GAN}$," and the similarity measure 412, such as represented by "$L_{SIM}$":

$$L = L_{GAN}(G,D) + \lambda \cdot L_{sim}(G) \qquad \text{EQN. 2}$$

The value "λ" can represent an adjustable weighting factor. In the expression of EQN. 2, and as shown below in EQN. 3, the term $L_{GAN}$ may include two terms. The first term can represent an expectation value that an input to the first discriminator including actual imaging data is identified as such by the first discriminator (e.g., "$E_{y \sim P_B(y)}[\log(D(y))]$", where "Ey" is the expectation value from the probability distribution "PB(y)" representing a distribution of actual imaging data used for training purposes as an input to the discriminator network, and "D(y)" represents operation of the discriminator network on the actual imaging data used for training) and the second term can represent an expectation value that an input to the discriminator including a synthesized image from the first generator is not identified as actual imaging data by the first discriminator (e.g., "$E_{x \sim P_A(x)}[\log(1-D(G(x)))]$", where "Ex" is the expectation value from a probability distribution "PA(x)" representing an input distribution of imaging data, "x," "G(x)" represents an operation of the generator network on the input imaging data to produce a synthetic image, and "D(G(x))" represents an operation of the discriminator network on the synthetic image provided by the generator network), as shown below in EQN. 3:

$$L_{GAN}(G,D) = E_{x \sim P_A(x)}[\log(1-D(G(x)))] + E_{y \sim P_B(y)}[\log(D(y))] \qquad \text{EQN. 3}$$

The similarity measure 412 can be represented as shown below in EQN. 4:

$$L_{sim}(G) = -E_{x \sim P_A(x)}[Sim(x, G(x))] \qquad \text{EQN. 4}$$

The term "Sim(x, G (x))" can represent to a similarity function indicative of a similarity between two images having different modalities (e.g., an input image, "x" and a synthesized image, "G(x)", provided by the generator 420) Inter-modality image similarity metrics are generally available and may include use of techniques comprising one or more of mutual information, normalized mutual information, cross-correlation, local cross-correction, or other techniques. Use of a cross-modality similarity function enables the training architecture 400 of FIG. 4 to be used with unpaired imaging data. The approach shown in FIG. 4 is not the only approach that could be used. By contrast with the approach shown in FIG. 4, training of an image synthesis or image modality translation model may be performed using a "CycleGAN" approach, using unpaired imaging data. But such an approach may present drawbacks, because generally in a CycleGAN approach, two image synthesis models are trained contemporaneously, including a first synthesis model (e.g., similar to $G_1$) to translate from a first imaging modality type to a second imaging modality type, and a second synthesis model to translate from the second imaging modality type back to the first imaging modality type. In addition, such a CycleGAN approach generally requires training of two "discriminators" contemporaneously. Training two models is unnecessary, and consumes significantly greater resources in terms of processing and memory consumption. The architecture 400 shown in FIG. 4 and described generally in this document provides a simpler adversarial network architecture as compared to CycleGAN, and the techniques described herein may still be trained using unpaired imaging data.

The imaging data used for training in relation to the architecture 400 shown in FIG. 4 may be site-specific, or may be obtained from a centralized repository, such as representative of multiple clinical sites. Such training information may include one or more variations such as relating to resolution, contrast, region imaged, imaging equipment type or manufacturer, or other variations, such as to help provide generator 420 parameters that are robust to such variations across one or more of patients, sites, or specific imaging equipment configuration.

Figure 5:
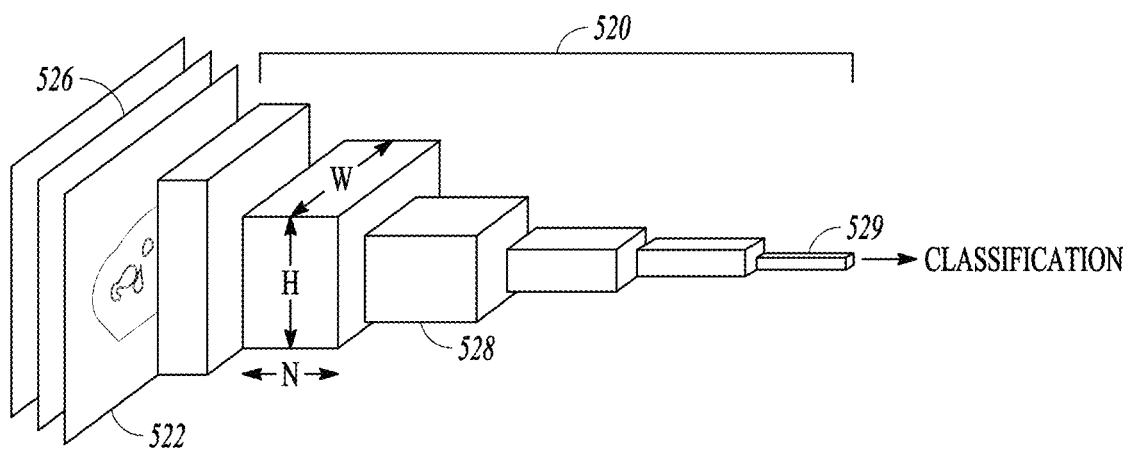
FIG. 5 illustrates an example including a statistical learning model (e.g., a convolutional neural network (CNN)), such as for performing classification of medical imaging data (e.g., for discrimination between synthesized imaging data and actual imaging data), such as may be used for training another statistical learning model to perform image synthesis.
Figure 6:
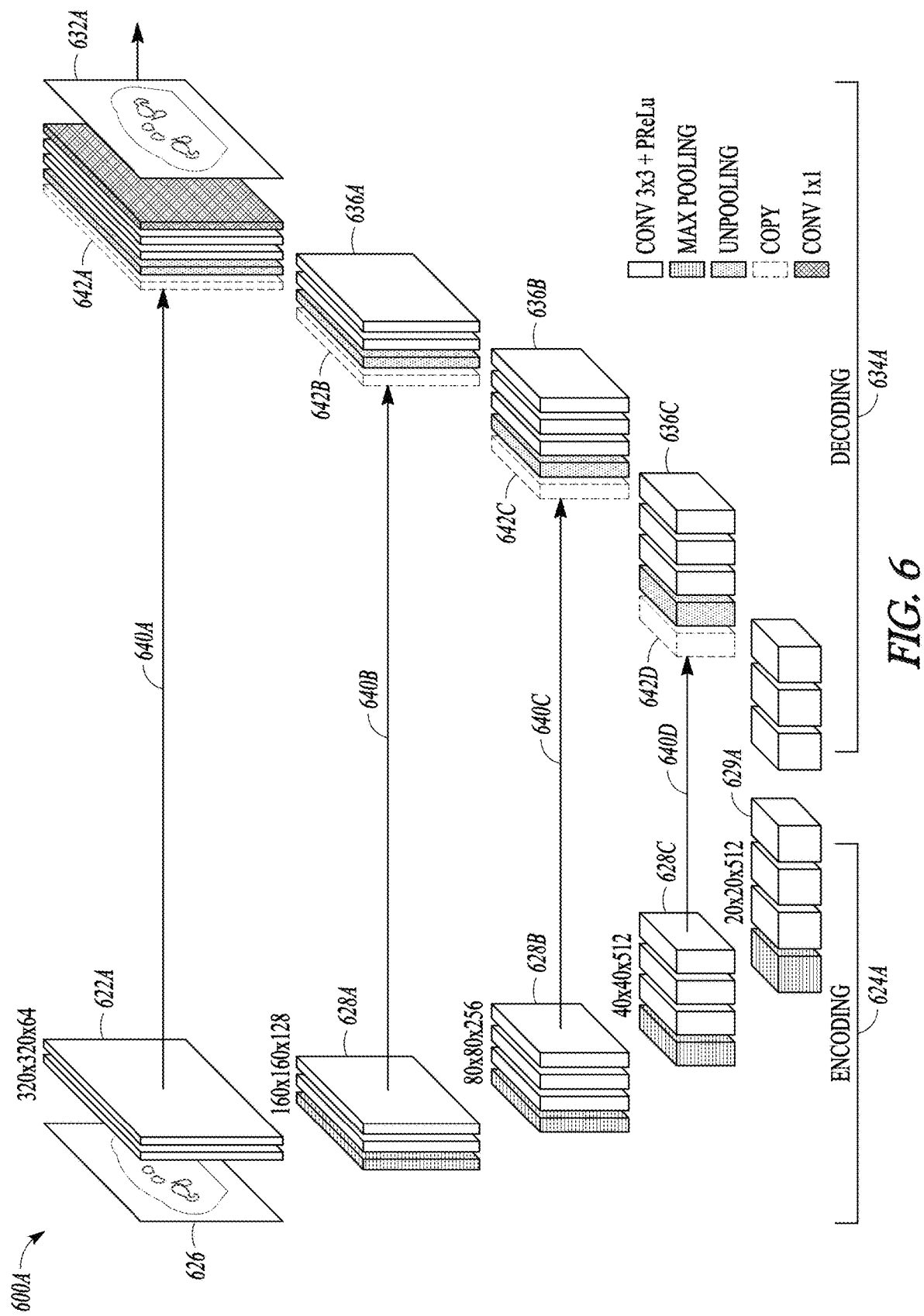
FIG. 6 illustrates an example including a statistical learning model (e.g., a convolutional neural network (CNN)), such as for receiving medical imaging data corresponding to a first imaging modality type and, using the received medical imaging data, performing synthesis of medical imaging data corresponding to a different second imaging modality type.

FIG. 5 illustrates an example including a statistical learning model (e.g., a convolutional neural network (CNN) 520), such as for performing classification of medical imaging data (e.g., for discrimination between synthesized imaging data and actual imaging data), such as may be used for training another statistical learning model to perform image synthesis. As shown in FIG. 5, a CNN model 520 for image classification may receive an image 522 as an input, from amongst one or more images 526 provided for purposes of training a separate generator convolutional neural network.

The CNN 520 may be trained using various approaches, such as discussed above in relation to FIG. 4 or elsewhere herein.

The classification output 529 from the CNN model 520 may be established using a series of one or more convolutional layers 528. Each convolutional layer 528 may have a plurality of parameters, such as the width ("W") and height ("H") determined by the upper input layer (e.g., the size of the input of convolutional layer 528), and a count of filters or kernels ("N") in the layer and their sizes. The number of filters may be referred to as the channels of a particular convolutional layer. Therefore, each convolutional layer 528 may be represented in terms of a 3D volume as shown in FIG. 5, however such a representation is merely illustrative. The input of each convolutional layer 528 is generally convolved with one filter across its width and height and produces a 2D activation map or feature map corresponding to that filter. The convolution is performed for all filters of each convolutional layer, and the resulting activation maps or feature maps are stacked along the channel dimension, generating a 3D output. The output of a preceding convolutional layer may be used as input to the next convolutional layer.

In some embodiments, the CNN model 520 includes one or more pooling layers. A pooling layer may be added between two successive convolutional layers 528 in CNN model 510. A pooling layer may operate independently on every channel of its input (e.g., an activation map or feature map from a previous convolutional layer), and reduces the spatial dimension by performing a form of non-linear downsampling. In certain examples, information from a non-adjacent layer may "skip" intervening layers and may be aggregated together with the output of a later convolutional layer before passing through a pooling layer, as discussed in relation to FIG. 6. As shown in FIG. 5, a function of the pooling layers may include progressively reducing a spatial dimension of the extracted activation maps or feature maps to reduce a count of parameters and computation in the network, and to control over-fitting. A count and placement of the pooling layers may be determined based on various factors, such as the configuration of the convolutional network architecture, the size of the input, the size of convolutional layers 528, or application of CNN model 520.

Various non-linear functions may be used to implement the pooling layers. For example, max pooling may be used. Max pooling may partition an image slice of the input into a set of overlapping or non-overlapping sub-regions with a predetermined stride. For each sub-region, max pooling outputs a maximum value amongst corresponding sub-regions within the partition. This effectively downsamples every slice of the input along both its width and its height while the channel dimension remains unchanged. Other suitable functions may be used for implementing the pooling layers, such as average pooling or even L2-norm pooling.

The CNN model 520 may selectively include one or more additional layers. As a non-limiting example, a Rectified Linear Unit (ReLu) layer or Parametric ReLU (PReLU) may be selectively added after a convolutional layer to generate an intermediate activation map or feature map. For example, a ReLu layer may desirably increase the nonlinear properties of the predictor function and the overall of CNN model 520 without affecting the respective dimensions of convolutional layers 528. Additionally, the ReLu layer may reduce or avoid saturation during a backpropagation training process.

As mentioned above, a classification output 529 from the CNN be a classification value, such as a value between zero and one, with one representing a determination that an input image 522 to the CNN model 520 represents an actual image, and zero representing a determination that the input image 522 is a "fake" synthesized by a separate generator statistical learning model.

FIG. 6 illustrates an example including a statistical learning model (e.g., a convolutional neural network (CNN) 600A), such as for receiving medical imaging data (e.g., a first image 626) corresponding to a first imaging modality type and, using the received medical imaging data, performing synthesis of medical imaging data (e.g., to provide a second image at output layer 632A) corresponding to a different second imaging modality type. The example of FIG. 6 may be used to provide the "generator" model mentioned in relation to the example of FIG. 4. Referring back to FIG. 6, the CNN 600A may be classified as a "fully convolutional neural network" (FCNs). Different FCN architectures may be used, such as having an encoding portion 624A. The encoding portion resembles a typical CNN that extracts a hierarchy of image features from low to high complexity. A decoding portion 634A then transforms the features and gradually reconstructs a synthetic image from coarser to finer resolution.

The architecture of the CNN 600A shows long-range connections 640A, 640B, and 640C. Short-range connections may also be used, such as within the encoding portion 624A or within the decoding portion 634A. Use of long range connections across the encoding and decoding portions (e.g., between portions 624A and 634A in FIG. 6) permits higher resolution features from the encoding portion (624A) to be used as inputs for (de)convolutional layers in the decoding portions (634A). Such a configuration enhances a capability of the decoding portion (634A) to generate high resolution predictions. These sorts of shortcuts also make the model 600A more flexible. For example, the model 600A may automatically through training learn to skip coarse level features (at the "bottom" of the network such as at layer 629A in FIG. 6) if high resolution features (at the "top" of the network) are sufficient to produce accurate synthesis. The long-range connections 640A, 640B, 640C, and 640D shown in FIG. 6 may be provided by taking an output of a corresponding convolutional layer to provide a corresponding copy 642A, 642B, 642C, and 642E, respectively.

Referring to the CNN 600A of FIG. 6, input imaging data may be provided to a first convolutional layer, such as having a spatial size of 320×320 and the convolutional layer may include 64 filters or "channels." The input stack may represent training images or a series of images to be translated. The CNN 600A of FIG. 6 may include five different resolution layers, such as a first downsampled layer 628A having an output size of 160×160×128 channels, a second downsampled layer 628B having an output size of 80×80× 256 channels, a third downsampled layer 628C having an output size of 40×40×512 layers, and a bottom layer 629A having an output size of 20×20×512 channels. An output of the bottom layer 629A may include feature-domain information (e.g., a feature map or feature vector set). Other counts of layers or channels, or different resolutions may be used.

Downsampling may be achieved through pooling as mentioned above in relation to FIG. 5. The decoding portion 634A of the CNN 600A of FIG. 6 may include upsampling or "deconvolutional" layers, such as a first upsampling layer 636C, a second upsampling layer 636B, and a third upsampling layer 636A. A final or output layer 632A may provide a synthesized image having a resolution similar to or matching a resolution of the input 2D imaging data. Consistent with various embodiments of the present disclosure, the image segmentation methods, systems, devices, or processes based on the above-described CNN models include two stages: a training phase that trains the CNN model using training datasets, and an image synthesis phase (e.g., run-time phase) that uses the trained CNN model to synthesis images having a different modality type than the input images.

Figure 7:
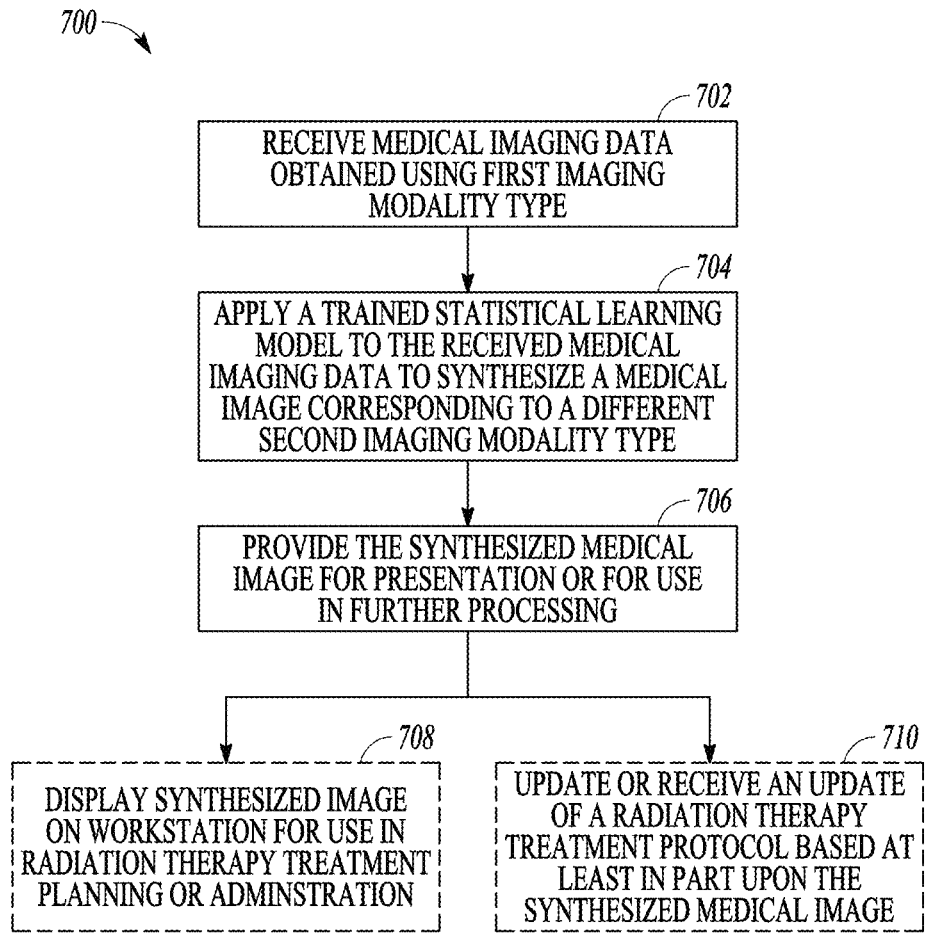
FIG. 7 illustrates generally a technique, such as a method, that may be computer-implemented, such as for performing synthesis of medical imaging data using a statistical learning model.

FIG. 7 illustrates generally a technique 700, such as a method, that may be computer-implemented, such as for performing synthesis of medical imaging data using a statistical learning model. At 702, medical imaging data may be obtained using a first imaging modality type. As mentioned in relation to other examples described in this document, such imaging data may be obtained directly from a connected imaging device such as an MR scanner, or such imaging data may be obtained from a medical imaging database. At 704, a trained statistical learning model may be applied to the received medical imaging data to synthesize a medical image corresponding to a different second imaging modality type. Such a learning model may include a generator convolutional neural network having parameters established using an adversarial training approach as described elsewhere herein (e.g., in FIG. 4 and FIG. 8). At 706, the synthesized medical image may be presented, either for display to a user or for use in further processing. For example, optionally, at 708, the synthesized image may be displayed on a workstation for use in radiation therapy treatment planning or administration. In an example, optionally, at 710, updating or receiving of an update of a radiation therapy treatment protocol may be performed, such as based at least in part upon the synthesized medical image.

Figure 8:
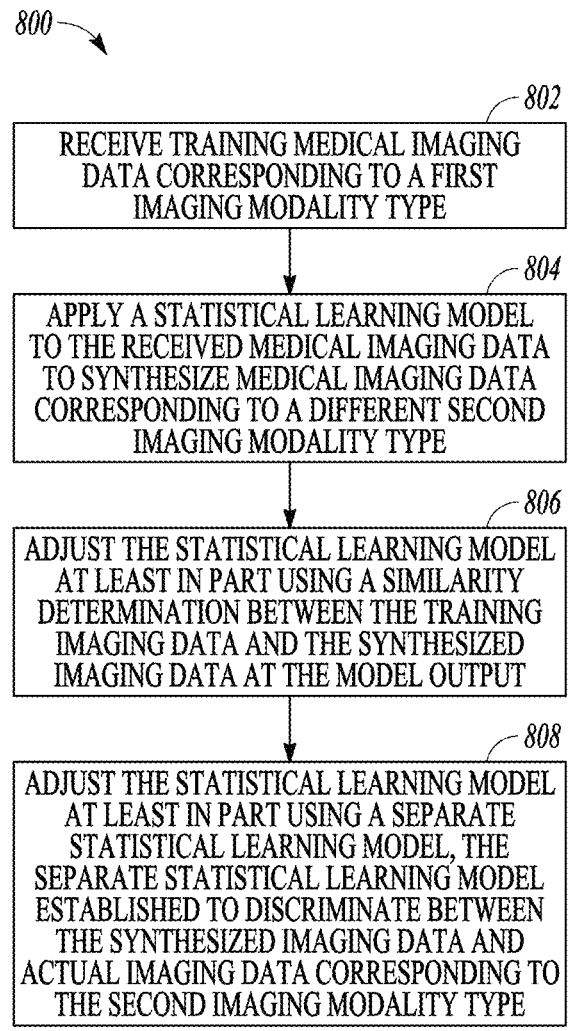
FIG. 8 illustrates generally a technique, such as a method, that may be computer-implemented, such as for implementing an adversarial training architecture to establish a statistical learning model for performing synthesis of medical imaging data.

FIG. 8 illustrates generally a technique 800, such as a method, that may be computer-implemented, such as for implementing an adversarial training architecture to establish a statistical learning model for performing synthesis of medical imaging data. At 802, training medical imaging data may be received, such as data corresponding to a first imaging modality type. As mentioned elsewhere, such training data may be site specific, or may be representative of a broader range of imaging device configurations, settings, patients, or sites, for example. At 804, a statistical learning model (e.g., a generator model for image synthesis) may be applied to the received medical image data to synthesize medical imaging data corresponding to a different second imaging modality type. At 806, the statistical learning model used to synthesize the medical imaging data at 804 may be adjusted, such as at least in part using a similarity determination between the training imaging data and the synthesized imaging data at the model output. At 808, the statistical learning model used to synthesize the medical imaging data at 804 may also be adjusted using a separate statistical learning model (e.g., a discriminator model for classification of imaging data). For example, the separate statistical learning model may be established to discriminate between synthesized imaging data and actual imaging data corresponding to the second imaging modality type. Again, the actual imaging data used for establishing the discriminator model may be site specific, or may be representative of a broader range of imaging device configurations, settings, patients, or sites, for example.

FIG. 9A, FIG. 9B, and FIG. 9C show illustrative examples comprising views (axial, sagittal, and coronal, respectively) of imaging data corresponding to a first imaging modality type (e.g., MR imaging data). FIG. 10A, FIG. 10B, and FIG. 10C show illustrative examples comprising views of synthesized imaging data corresponding to a second imaging modality type (e.g., CT imaging), the synthesized imaging data provided using a statistical learning model (e.g., a deep convolutional neural network comprising a generator model) applied to the imaging data of FIG. 9A, FIG. 9B, and FIG. 9C, respectively. FIG. 11A, FIG. 11B, and FIG. 11C show illustrative examples comprising views of actual imaging data obtained using the second imaging modality type (e.g., CT imaging), presented herein for comparison with the synthesized imaging data of FIG. 10A, FIG. 10B, and FIG. 10C, respectively, and showing that the synthesized images correspond well with the "ground truth" images of FIG. 11A, FIG. 11B, and FIG. 11C.

Various Notes

Each of the non-limiting described in this document above may stand on its own, or may be combined in various permutations or combinations with one or more of the other aspects or other subject matter described in this document.

The above detailed description includes references to the accompanying drawings, which form a part of the detailed description. The drawings show, by way of illustration, specific embodiments in which the invention may be practiced. These embodiments are also referred to generally as "examples." Such examples may include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the invention should be determined with reference to the appended claims, along with the full scope of equivalents to which such claims are entitled.

The claimed invention is:

1. A computer-implemented method for synthesizing a medical image using a trained statistical learning model, the method comprising:
   receiving medical imaging data obtained using a first imaging modality type;
   applying the trained statistical learning model to the received medical imaging data to synthesize a medical image corresponding to a different second imaging modality type; and
   providing the synthesized medical image for presentation or for use in further processing;
   wherein the trained statistical learning model is established using a similarity determination between training imaging data provided at the model input without reconstructing an image of the first imaging modality type, the training imaging data corresponding to the first imaging modality type and synthesized imaging data at the model output corresponding to the second imaging modality type; and
   wherein the trained statistical learning model is established at least in part using a single generator and a separate statistical learning model, the separate statistical learning model established to discriminate between actual imaging data corresponding to the second imaging modality and the synthesized imaging data.

2. The computer-implemented method of claim 1, wherein the single generator comprises a first generator convolutional network and the separate statistical learning model comprises a first discriminator convolutional network.

3. The computer-implemented method of claim 2, wherein the trained statistical learning model is established without use of a second generator convolutional network and a second discriminator convolutional network, the second generator convolutional network trained to synthesize a medical image corresponding to the first imaging modality type from an input image corresponding to the second imaging modality type, and the second discriminator network established to discriminate between synthesized imaging data corresponding to the first imaging modality type and actual imaging data corresponding to the first imaging modality type.

4. The computer-implemented method of claim 2, wherein the first generator convolutional network and the first discriminator convolutional network form an adversarial network architecture, the adversarial network architecture structured to:
   adjust the first discriminator convolutional network to enhance or maximize a value of an objective over a distribution of inputs to the first discriminator convolutional network; and
   adjust the first generator convolutional network to reduce or minimize the value of the objective over a distribution of inputs to the first generator convolutional network.

5. The computer-implemented method of claim 4, wherein the objective is represented as a sum of contributions from an adversarial objective and the similarity determination.

6. The computer-implemented method of claim 4, wherein the objective comprises terms representing (1) an expectation value that an input to the first discriminator including actual imaging data is identified as such by the first discriminator and (2) an expectation value that an input to the discriminator including a synthesized image from the first generator is not identified as actual imaging data by the first discriminator.

7. The computer-implemented method of claim 1, wherein the similarity determination comprises at least one of: a mutual information determination; or a cross-correlation determination.

8. The computer-implemented method of claim 1, wherein the first imaging modality type comprises magnetic resonance (MR) imaging; and
   wherein the second imaging modality type comprises computed tomography (CT) imaging.

9. The computer-implemented method of claim 1, wherein presenting the synthesized image includes displaying the image on an MR-LINAC workstation for use in radiation therapy treatment planning or administration.

10. The computer-implemented method of claim 1, comprising updating, or receiving an update, of a radiation therapy treatment protocol based at least in part upon the synthesized medical image.

11. A computer-implemented method for establishing a trained statistical learning model for synthesizing a medical image without requiring paired imaging for training, the method comprising:
    receiving training medical imaging data corresponding to a first imaging modality type;
    applying a statistical learning model to the received medical imaging data to synthesize imaging data corresponding to a different second imaging modality type;
    adjusting the statistical learning model using a similarity determination between the training imaging data and synthesized imaging data at the model output without reconstructing an image of the first imaging modality type; and adjusting the statistical learning model using a single generator and a separate statistical learning model, the separate statistical learning model established to discriminate between the synthesized imaging data and actual imaging data corresponding to the second imaging modality type.

12. The computer-implemented method of claim 11, wherein the single generator comprises a first generator convolutional network and the separate statistical learning model comprises a first discriminator convolutional network.

13. The computer-implemented method of claim 12, wherein adjusting the statistical learning model includes using a stochastic gradient descent technique.

14. The computer-implemented method of claim 12, wherein the first generator convolutional network and the first discriminator convolutional network form an adversarial network architecture, the adversarial network architecture structured to:

adjust the first discriminator convolutional network to enhance or maximize a value of an objective over a distribution of inputs to the first discriminator convolutional network; and adjust the first generator convolutional network to reduce or minimize the value of the objective over a distribution of inputs to the first generator convolutional network.

15. The computer-implemented method of claim 14, wherein the objective is represented as a sum of contributions from an adversarial objective and the similarity determination.

16. The computer-implemented method of claim 14, wherein the objective comprises terms representing (1) an expectation value that an input to the first discriminator including actual imaging data is identified as such by the first discriminator and (2) an expectation value that an input to the discriminator including a synthesized image from the first generator is not identified as actual imaging data by the first discriminator.

17. The computer-implemented method of claim 11, wherein the similarity determination comprises at least one of: a mutual information determination; or a cross-correlation determination.

18. The computer-implemented method of claim 11, wherein the first imaging modality type comprises magnetic resonance (MR) imaging; and wherein the second imaging modality type comprises computed tomography (CT) imaging.

19. A system, comprising:

processing circuitry comprising at least one processor; and a storage medium comprising instructions, which when executed by the at least one processor, cause the processor to:

receive medical imaging data obtained using a first imaging modality type;

apply the trained statistical learning model to the received medical imaging data to synthesize a medical image corresponding to a different second imaging modality type; and provide the synthesized medical image for presentation or for use in further processing;

wherein the trained statistical learning model is established using a similarity determination between training imaging data provided at the model input without reconstructing an image of the first imaging modality type, the training imaging data corresponding to the first imaging modality type and synthesized imaging data at the model output corresponding to the second imaging modality type; and wherein the trained statistical learning model is established using a single generator and a separate statistical learning model, the separate statistical learning model established to discriminate between the synthesized imaging data and actual imaging data corresponding to the second imaging modality type.

20. The system of claim 19, wherein the instructions cause the processor to update, or receive an update, of a radiation therapy treatment protocol based at least in part upon the synthesized medical image.

* * * * *